(12) United States Patent
Graessl et al.

(10) Patent No.: US 10,309,914 B2
(45) Date of Patent: Jun. 4, 2019

(54) USE OF A MEASURING APPLIANCE FOR EXAMINING FUEL, OIL AND/OR HYDRAULIC FLUID

(71) Applicant: Robert Bosch GmbH, Stuttgart (DE)

(72) Inventors: Andreas Graessl, Leinfelden-Echterdingen (DE); Klaus Marx, Stuttgart (DE); Reiner Krapf, Filderstadt (DE); Ulli Hoffmann, Niefern-Oeschelbronn (DE)

(73) Assignee: Robert Bosch GmbH, Stuttgart (DE)

( * ) Notice: Subject to any disclaimer, the term of this patent is extended or adjusted under 35 U.S.C. 154(b) by 153 days.

(21) Appl. No.: 15/385,332

(22) Filed: Dec. 20, 2016

(65) Prior Publication Data

US 2017/0176359 A1    Jun. 22, 2017

(30) Foreign Application Priority Data

Dec. 21, 2015 (DE) .................. 10 2015 226 179

(51) Int. Cl.
*G01V 3/00* (2006.01)
*G01N 24/08* (2006.01)
(Continued)

(52) U.S. Cl.
CPC ............ *G01N 24/08* (2013.01); *G01N 33/28* (2013.01); *G01R 33/3808* (2013.01); *G01N 33/22* (2013.01); *G01R 33/448* (2013.01)

(58) Field of Classification Search
CPC .... G01N 24/08; G01N 24/081; G01N 24/082; G01N 24/084; G01N 15/08;
(Continued)

(56) References Cited

U.S. PATENT DOCUMENTS 3,242,667 A * 3/1966 Kidwell, Jr. ............ C06B 43/00
                                                          149/22
7,355,402 B1 * 4/2008 Taicher .................. G01R 33/44
                                                          324/300
(Continued)

FOREIGN PATENT DOCUMENTS

DE    10 2014 218 371 A1    3/2016
DE    10 2014 218 375 A1    3/2016
(Continued)

OTHER PUBLICATIONS

Luis F. Cabeca et al., "Monitoring the Transesterification Reaction Used in Biodiesel Production, with a Low Cost Unilateral Nuclear Magnetic Resonance Sensor", Energy & Fuels, May 2011, pp. 2696-2701, vol. 25, No. 6, ACS Publications.
(Continued)

*Primary Examiner* — Walter L Lindsay, Jr.
*Assistant Examiner* — Frederick Wenderoth
(74) *Attorney, Agent, or Firm* — Maginot, Moore & Beck LLP

(57) ABSTRACT

A hand-held measuring appliance includes at least a nuclear magnetic resonance sensor, a control apparatus configured to control the measuring appliance, an evaluation apparatus configured to evaluate a measurement signal supplied by the nuclear magnetic resonance sensor, an output apparatus configured to output ascertained information, and an apparatus for energy supply. The measuring appliance is configured to examine at least one of fuel, oil, and hydraulic fluid.

9 Claims, 9 Drawing Sheets

(51) Int. Cl.
  *G01N 33/28* (2006.01)
  *G01R 33/38* (2006.01)
  *G01R 33/44* (2006.01)
  *G01N 33/22* (2006.01)

(58) Field of Classification Search
  CPC .... G01N 24/087; G01N 21/10; G01R 33/302; G01R 33/448; G01R 33/3808; G01R 33/465; G01R 33/28; G01R 33/30; G01R 33/307; G01R 33/34007; G01R 33/46; G01R 33/543; G01R 33/5659; G01R 33/3415; G01R 33/36; A61B 5/055
  USPC .......................................................... 324/309
  See application file for complete search history.

(56) References Cited

U.S. PATENT DOCUMENTS

| | | | |
|---|---|---|---|
| 2005/0024055 A1* | 2/2005 | Cavaluzzi | G01R 33/30 324/321 |
| 2007/0152669 A1* | 7/2007 | Park | B82Y 30/00 324/321 |
| 2007/0152670 A1* | 7/2007 | Park | B82Y 30/00 324/321 |
| 2011/0091987 A1* | 4/2011 | Weissleder | G01R 33/302 436/173 |
| 2014/0194715 A1* | 7/2014 | Griswold | A61B 5/14532 600/365 |
| 2015/0253264 A1* | 9/2015 | Prado | G01N 24/082 324/309 |
| 2016/0003753 A1* | 1/2016 | Augustine | G01N 24/084 324/309 |
| 2016/0178398 A1* | 6/2016 | Krapf | B25F 5/00 429/90 |
| 2017/0102344 A1* | 4/2017 | Lei | G01N 24/08 |
| 2017/0115242 A1* | 4/2017 | Kwak | G01N 15/08 |
| 2017/0123098 A1* | 5/2017 | Wang | G01V 3/38 |
| 2017/0153350 A1* | 6/2017 | Krapf | G01V 3/17 |
| 2017/0176549 A1* | 6/2017 | Krapf | G01R 33/28 |
| 2017/0261443 A1* | 9/2017 | Krapf | G01N 24/08 |
| 2017/0261444 A1* | 9/2017 | Krapf | G01N 24/08 |

FOREIGN PATENT DOCUMENTS

| | | |
|---|---|---|
| EP | 2 182 390 A2 | 5/2010 |
| GB | 2 404 026 A | 1/2005 |
| JP | 2011-80766 A | 4/2011 |
| WO | 2014/004573 A1 | 1/2014 |

OTHER PUBLICATIONS

R. S. Kashaev et al., "The Influence of Sulfur on the Structural-Dynamic Parameters of Petroleum Systems Studied by the NMR Technique", Petroleum Chemistry, Nov. 2009, pp. 507-511, vol. 49, No. 6, Pleiades Publishing, Ltd.

Meijuan Chen et al., "Investigation of the extraction process in gel-spinning technology for ultrahigh-molecular weight polyethylene fibers by low-field nuclear magnetic resonance", Journal of Applied Polymer Science, Feb. 2015, vol. 132, No. 23, Wiley Periodicals, Inc.

A. E. Pryakhin et al., "NMR Flowmeter for Proton-Bearing Liquids", Measurement Techniques, Nov. 1988, pp. 1092-1094, vol. 31, No. 11, Plenum Publishing Corporation.

* cited by examiner

USE OF A MEASURING APPLIANCE FOR EXAMINING FUEL, OIL AND/OR HYDRAULIC FLUID

This application claims priority under 35 U.S.C. § 119 to patent application no. DE 10 2015 226 179.4, filed on Dec. 21, 2015 in Germany, the disclosure of which is incorporated herein by reference in its entirety.

BACKGROUND

The present disclosure relates to the use of a measuring appliance, in particular a hand-held measuring appliance, comprising a nuclear magnetic resonance sensor.

DE 10 2014 218 375 A1 and DE 10 2014 218 371 A1 have disclosed measuring appliances, each with a sensor apparatus, wherein the sensor apparatus comprises at least one nuclear magnetic resonance sensor which is provided for determining a humidity value or for detecting and/or analyzing and/or distinguishing between material characteristics of a workpiece to be examined.

SUMMARY

According to the disclosure, the use of a measuring appliance, in particular a hand-held measuring appliance, preferably a measuring appliance comprising a housing, comprising at least
  a nuclear magnetic resonance sensor,
  a control apparatus for controlling the measuring appliance,
  an evaluation apparatus for evaluating a measurement signal supplied by the nuclear magnetic resonance sensor,
  an output apparatus for outputting ascertained information and
  an apparatus for energy supply,
for the purposes of examining a fuel and/or an oil and/or a hydraulic fluid is proposed.

In one embodiment, the measuring appliance constitutes a hand-held measuring appliance. Here, a "hand-held measuring appliance" should be understood to mean, in particular, that the measuring appliance may be transported without the aid of a transport machine and by using only hands, in particular one hand. The measuring appliance may in particular be guided on and/or along a fuel and/or oil and/or a hydraulic fluid to be examined and/or on and/or along a container (not repeatedly listed below), in which the corresponding liquid is contained, during a measuring process as well. To this end, the mass of the hand-held measuring appliance is in particular less than 20 kg, advantageously less than 10 kg and particularly advantageously less than 2 kg. In one embodiment, the measuring appliance has a handle or a handle region, by means of which the measuring appliance may be guided over a fuel to be examined and/or an oil to be examined and/or a hydraulic fluid to be examined or a corresponding container. Alternatively, or additionally, for the purposes of the examination thereof, the oil to be examined and/or the fuel and/or the hydraulic fluid or a corresponding container may also be guided on the measuring appliance and/or along the measuring appliance.

In one embodiment, the measuring appliance is used in a vehicle, in particular a motor vehicle. In an embodiment designed thus, the measuring appliance may have both a hand-held and stationary embodiment, for example an embodiment fixedly integrated or installed into the vehicle.

In one embodiment of the measuring appliance, the components of the measuring appliance, in particular the nuclear magnetic resonance sensor, the control apparatus, the evaluation apparatus and the apparatus for energy supply of the measuring appliance, are housed, at least in part, in the housing of the measuring appliance. In particular, the components are housed in the housing of the measuring appliance with more than 50%, preferably with more than 75% and particularly preferably with 100% in terms of the overall volume thereof. In a measuring appliance designed thus, an advantageous use may be realized, in particular by easy guidance, in the case of a hand-held measuring appliance. Moreover, the components are thus protected from damage and ambient influences, for example moisture and dust.

The measuring appliance comprises an apparatus for energy supply which is provided to supply the measuring appliance with electric energy for starting up purposes and during the operation. In one embodiment, the apparatus for energy supply is realized as a wired current supply using an external energy source, for example in the form of an electric connection to a circuit, a battery, in particular a vehicle battery, an alternator or the like. In this embodiment, the plug-in connection of the measuring appliance for connection with the external energy source, in particular also in conjunction with a transformer, constitutes an apparatus for energy supply. In one embodiment of this plug-in connection, the measuring appliance is detachable from the external energy source by means of an interlocking and/or force-fit connection interface from the plug-in connection. In this context, "detachable" should, in particular, be understood to mean separable in a non-destructive manner. Hence, the measuring appliance is preferably removable and/or decoupleable from the external energy source.

In an alternative or additional embodiment, the measuring appliance, in particular the hand-held measuring appliance, is realized as an energy-independent measuring appliance. "Energy-independent" should be understood to mean that the measuring appliance may be operated independently of a power grid, in particular in a wireless manner, at least on a temporary basis, preferably at least during the duration of an examination of a fuel and/or oil and/or a hydraulic fluid. To this end, the measuring appliance may comprise an apparatus for energy supply in the form of a power-grid-independent energy store, in particular in the form of a battery, preferably in the form of a rechargeable battery. In an alternative embodiment, the power-grid-independent energy store may also be realized as a fuel cell, a capacitor, a hybrid supercapacitor or as any other energy store appearing expedient to a person skilled in the art and/or a combination/plurality thereof. Accumulators with a cell chemistry providing a high power and/or energy density are particularly suitable for supplying the measuring appliance with energy. A high power and/or energy density permits an improved energy supply of the measuring appliance, in particular an energy supply with a longer service life and adapted to a high power requirement of the nuclear magnetic resonance sensor. Currently, these include e.g. accumulators with lithium and lithium ion cell chemistry, in particular lithium iron phosphate accumulators, lithium manganese oxide accumulators, lithium nickel cobalt manganese oxide accumulators, over-lithiated lithium nickel cobalt manganese oxide accumulators, lithium sulfur accumulators, lithium polymer accumulators and lithium oxygen accumulators. In this embodiment, the apparatus for energy supply may be realized to be detachable from the measuring appliance by way of an interlocking and/or force-fit connection interface. In this context, "detachable" should be understood to mean, in particular, separable in a non-destructive manner. Hence, the apparatus for energy supply is arrangeable on and/or in the measuring appliance, preferably in a removable and interchangeable manner. In the form of such an energy store, the removable apparatus for energy supply may be resupplied and charged with energy from a power grid when within and/or outside of the measuring appliance. In one embodiment of the apparatus for energy supply, the latter is provided also to be usable for supplying energy to other appliances, in particular other measuring appliances and/or other handheld machine tool apparatuses in addition to the use for supplying the measuring appliance with energy.

In particular, "provided" should be understood to mean, specifically, "programmed", "configured" and/or "equipped". An object being "provided" for a specific function should be understood to mean, in particular, that the object fulfills and/or carries out this specific function in at least one application and/or operating state, or it is configured to fulfill the function.

For the control thereof, the measuring appliance comprises a control apparatus. The control apparatus has a signaling connection with the other components of the measuring appliance, in particular the nuclear magnetic resonance sensor, the evaluation apparatus, the output apparatus, further e.g. also with an input apparatus, the apparatus for energy supply and/or a data communication interface. The control apparatus is provided to communicate with these components during the operation of the measuring appliance. In particular, a "control apparatus" should be understood to mean an apparatus with at least one control electronics element which comprises a means for communication with the other components of the measuring appliance, for example means for open-loop and/or closed-loop control of the nuclear magnetic resonance sensor, means for data processing, means for data storage and/or further means appearing expedient to a person skilled in the art. In one embodiment, the control electronics of the control apparatus should be understood to mean a processor unit in conjunction with a memory unit and an operating program stored in the memory unit, said operating program running during the control procedure. In particular, the electronic components of the control apparatus may be arranged on a circuit board (printed circuit board), for example in the form of a microcontroller.

The measuring appliance has a nuclear magnetic resonance sensor for the purposes of examining a fuel and/or oil and/or a hydraulic fluid. The functionality of the nuclear magnetic resonance sensor is based on the nuclear physics effect in which atomic nuclei in the oil and/or fuel to be examined absorb and emit alternating electromagnetic fields when in a first magnetic field denoted by $B_0$. Here, the nuclear magnetic resonance is based on the precession (Larmor precession) of nuclear spins of the atomic nuclei around the magnetic field lines of the first, in particular constant and/or static, magnetic field in the medium to be examined. In particular, the nuclear spins of the atomic nuclei in the oil and/or fuel and/or hydraulic fluid to be examined are aligned by the first magnetic field. If energy is radiated onto the atomic nuclei in the form of a second electromagnetic field, in particular in the form of an alternating field, for example a pulsed magnetic field, which is in resonance with the Larmor precession of the nuclear spins thereof (energy quanta), the atomic nuclei may change the orientation of their spins relative to the first magnetic field as a result of absorbing this energy. The second magnetic field radiated thereon therefore serves to excite the nuclear spins, which change their nuclear spin states under the reception of energy. Equivalently, the emission of energy quanta subsequently leads to the return of the excited nuclear spins to another, lower energy level and to the emission of an alternating electromagnetic field which may be observed by means of an apparatus for detecting a magnetic field change, in particular by means of an antenna and/or a coil. The atomic nuclei should be understood to mean, in particular, protons (H) and other nuclear magnetic resonance active nuclei such as e.g. 13C, 15N, 19F or 31P.

Therefore, the nuclear magnetic resonance sensor of the measuring appliance allows the excitation of atomic nuclei by means of alternating electromagnetic fields in the oil and/or fuel to be examined and/or the hydraulic fluid to be examined and the generation of an output signal on account of a nuclear magnetic resonance effect. In particular, excitation of atomic nuclei should be understood to mean that the energy of the electromagnetic fields radiated thereon, in particular alternating fields, causes a change in the nuclear spins of the atomic nuclei. It should be noted that the assumption is made below that, in particular, varying magnetic fields are coupled to electric fields (cf. Maxwell's equations) and so no distinction is made between an electric field and a magnetic field. What is important for the excitation of nuclear magnetic resonance effects is the energy transferred by way of electromagnetic radiation radiated thereon. In one embodiment, this energy may be transferred by means of pulsed electromagnetic fields.

If the operating parameters of the nuclear magnetic resonance sensor are suitably selected, it is possible to immediately deduce the oil and/or the fuel and/or the hydraulic fluid and the properties thereof, at least in an examined volume, in the case of a suitable evaluation by means of the measured response signal using the measuring appliance. Here, for example, the properties may relate to the quality, origin, authenticity or the like of the fluid and/or oil and/or the hydraulic fluid.

The "evaluation apparatus" for evaluating at least one measurement signal supplied by the nuclear magnetic resonance sensor should be understood to mean at least one apparatus which comprises an information input for receiving the measurement signals from the nuclear magnetic resonance sensor, an information processing unit for processing, in particular evaluating, the received measurement signals, and an information output for forwarding the processed and/or evaluated measurement signals. In one embodiment, the evaluation unit has components which comprise at least one processor, a memory and an operating program with evaluation and calculation routines. In particular, the electronic components of the evaluation apparatus may be arranged on a circuit board (printed circuit board), in particular on a common circuit board with the control apparatus. In one embodiment, the evaluation apparatus may be realized in the form of a microcontroller. Furthermore, the control apparatus and the evaluation apparatus may be embodied as a single component. The evaluation apparatus is provided to evaluate the measurement signals obtained by the nuclear magnetic resonance sensor and to derive at least information in relation to the examined oil and/or the examined fuel and/or the examined hydraulic fluid therefrom.

The "output apparatus" of the measuring appliance should be understood to mean at least one component of the measuring appliance which serves for the communication of the measuring appliance with the external surroundings, for example external appliances, humans or the like. During the communication, there is an output of information in the form of an electric voltage, current, acoustic sound, electromagnetic waves, data or the like. In this way, the output apparatus may, in particular, be realized as a data interface (referred to as "data communication interface" below) and/or as a user interface between human and appliance (referred to below as "output apparatus for output to an operator" of the measuring appliance).

In one embodiment of the measuring appliance, in particular in the case of a hand-held measuring appliance, the output apparatus should be understood to mean, for example, a means which is provided to output at least one varying information item to an operator in an acoustic, optical and/or tactile manner. Here, the output apparatus serves to output to the operator of the measuring appliance at least that information which is obtained using the measuring appliance about the examined oil and/or about the examined fuel and/or about the examined hydraulic fluid. By way of example the output may in this case be realized by means of a display, a touch display, a sound signal, a vibration transducer and/or an LED display. In one embodiment of the output apparatus for output to an operator, the information may be output graphically or alphanumerically as a measurement result of the examination. In one embodiment, the output apparatus is housed in a housing of the measuring appliance.

Furthermore, information to be output, for example information about an examined oil and/or fuel and/or about an examined hydraulic fluid, may also be output to the control apparatus and/or to a data-processing system, in particular for increasing user convenience. The latter comprises at least one information output to an external appliance such as a smartphone, a tablet PC, a PC and any other external data appliance appearing expedient to a person skilled in the art such as e.g. a motor controller or the like, which external data appliance is connected to the evaluation apparatus and/or the control apparatus of the measuring appliance by way of a data communication interface. Here, the data communication interface serves for communication, in particular wireless communication, by means of which the measuring appliance may transmit and/or receive measurement signals, evaluated information and/or working parameters. Preferably, the data communication interface uses a standardized communication protocol for transferring electronic data, in particular digital data. In one embodiment, the data communication interface comprises a wireless interface, in particular e.g. a WLAN interface, Bluetooth interface, infrared interface, NFC interface, RFID interface, GSM interface or any other wireless interface appearing expedient to a person skilled in the art. Alternatively, the data communication interface may also comprise a wired adapter, for example a network adapter, USB adapter or micro-USB adapter. Furthermore, a transfer of reference data which may be usable for evaluating and/or interpreting measurement signals captured by the measuring appliance may be facilitated using the data communication interface. The reference data here are in particular recalled from an appliance-internal and/or appliance-external reference database. Furthermore, multifaceted additional functions may advantageously be facilitated and included, said additional functions, in particular, also requiring direct communication with smartphones (in particular by way of programmed apps) or similar portable data appliances. By way of example, these may comprise automatic mapping functions, firmware updates, data post-processing, data preparation, data comparison with other appliances, etc.

Hence, the output apparatus may be housed directly in the housing of the measuring appliance, particularly in the case of a hand-held measuring appliance, and/or may be realized or complemented by external output apparatuses, particularly in the case of a stationary measuring apparatus. The latter realization option explicitly comprises the control, evaluation and output of the ascertained information to or by way of wired and/or wireless external systems such as, for example, remote controls, computer controls, tablet PCs, cellular telephones, smartphones, and/or other appliances such as control appliances or the like.

In accordance with the chemical definition, "oil" should, in particular, be understood to mean any type of liquid which cannot be mixed with water. In one embodiment, this may be, in particular, mineral oil, crude oil, heating oil, diesel oil, heavy oil, synthetic oil or the like. In particular, oil should also be understood to mean hydraulic fluids such as e.g. brake fluid and lubricants, with the latter being particularly suitable for lubricating mechanical components such as a combustion engine. Here, "fuel" should be understood to mean a liquid or gaseous fuel for driving vehicles—for example motor vehicles, airplanes, ships or the like. Here, the fuel serves to provide chemically bound energy. Here, the chemically bound energy may be converted into mechanical energy as a consequence of combustion—for example in internal combustion engines such as combustion motors or the like. Typical examples of such a fuel include diesel, petrol, kerosene, ethanol fuel, liquefied natural gas, liquefied petroleum gas, benzene or the like.

In particular, "use for examining a fuel and/or oil and/or a hydraulic fluid" should be understood to mean the determination of information from the measurement signals obtained from the nuclear magnetic resonance sensor using the measuring appliance and, hence, the derivation of statements relating to the properties and, in particular, the state of an oil and/or a fuel and/or a hydraulic fluid. In particular, in the case of a suitable evaluation of the measurement signals from the nuclear magnetic resonance sensor, it is possible to ascertain information in respect of origin (composition, chemical treatment), in respect of quality (water distribution, water content, aging state, contaminants, composition, viscosity, porosity), in respect of content (content detrimental to health, prohibited content, metal content, declared content) or the like. Hence, using this evaluated information (also referred to as "evaluation results" below), an operator of the measuring appliance and/or an external appliance supplied with information from the measuring appliance may examine and test the quality, origin, authenticity, viscosity, porosity or the like of the fuel and/or the oil and/or the hydraulic fluid in a simple manner. Furthermore, the obtained information may be compared to the producer specifications in relation to the examined oil and/or fuel and/or the examined hydraulic fluid and hence the authenticity thereof may be checked. Manipulations, fakes, incorrect labeling or the like may easily be uncovered by a brief examination of the fuel and/or oil and/or the hydraulic fluid.

In order to carry out the measurement, the measuring appliance, in particular the hand-held measuring appliance, in particular the nuclear magnetic resonance sensor thereof, is brought into the vicinity of the oil to be examined and/or the fuel to be examined and/or the hydraulic fluid to be examined (or the container thereof), or vice versa. Here, the use of the measuring appliance allows the examination without impairment of the fuel and/or oil and/or the hydraulic fluid, i.e., in particular, without destruction, contamination or the like. In particular, the nuclear magnetic resonance measuring method is a non-destructive, in particular contactless measuring method, and so an oil and/or a fuel and/or a hydraulic fluid may be examined without any contact with the measuring appliance. Positioning the measuring appliance, in particular the nuclear magnetic resonance sensor contained therein, in the direct vicinity of a fuel and/or oil to be examined and/or a hydraulic fluid to be examined (or vice versa) facilitates the examination up to a material depth of a few centimeters into the oil and/or into the fuel and/or into the hydraulic fluid. Hence, there may likewise be an examination of a packaged/enclosed oil and/or fuel and/or hydraulic fluid without destroying or opening the container. In one embodiment, an oil and/or a fuel and/or a hydraulic fluid may likewise be examined in a closed system, for example in a tube system of a circulation in a motor, without destroying or opening the system.

The measuring appliance, in particular the hand-held measuring appliance, represents a special measuring appliance which, in comparison with scientific nuclear magnetic resonance measuring appliances, has a greatly restricted functionality which is optimized to the examination of a fuel and/or an oil and/or a hydraulic fluid. In particular, the evaluation apparatus with the evaluation routines thereof is tailored to the examination of oil and/or fuel and/or hydraulic fluid, the evaluation of the information contained therein and the prepared output thereof by means of the output apparatus. When using the measuring appliance for examining fuel and/or oil and/or hydraulic fluid, the measurement results, i.e. the obtained information, are prepared for the operator of the measuring appliance and/or for a further external appliance (e.g. a motor controller or a brake booster controller) in an appliance-internal manner immediately after the measurement such that a quick and unique assessment of the examined fuel and/or oil and/or the examined hydraulic fluid is possible in situ, said assessment, in particular, being independent of further appliances such as computers or even of laboratories. Advantageously, a simple and intuitive operation of the measuring appliance which does not require particular previous experience of the operator is achievable.

Moreover, the installation size, energy supply and structure of the measuring appliance are adapted in respect of the arrangement of the nuclear magnetic resonance sensor to use of the measuring appliance for examining oil and/or fuel and/or hydraulic fluid. Thus, the measuring appliance, in one embodiment, particularly in the case of a hand-held measuring appliance, has e.g. a planar support surface, against which an oil and/or fuel and/or a hydraulic fluid may be placed for examination purposes. In an alternative or additional embodiment of the hand-held measuring appliance, the latter has, in the housing, a receptacle for an oil sample and/or fuel sample and/or hydraulic fluid sample, for example for a container in the form of a can, a bottle and/or a sample tube. In one embodiment, this receptacle may have a round and/or cylindrical and/or C-shaped configuration.

In one configuration, the measuring appliance is used for examining a fuel and/or oil and/or a hydraulic fluid in a vehicle, in particular in a motor vehicle, preferably during operation of the vehicle. In this manner, the measuring appliance integrated into a vehicle may ascertain information in relation to an oil and/or a fuel and/or a hydraulic fluid during operation of the vehicle. In one embodiment, an examination of the oil and/or of the fuel may, for example, be carried out in real time. In one embodiment of the measuring appliance, the examination, i.e. measuring, evaluating and outputting obtained information, is carried out fully automatically.

In one configuration, the measuring appliance is used directly on a fuel-conducting and/or oil-conducting and/or hydraulic-fluid-conducting component of the vehicle for the purposes of examining a fuel and/or an oil and/or a hydraulic fluid. To this end, the measuring appliance may advantageously be provided in a pipe or a tube or in another fuel-conducting and/or oil-conducting and/or hydraulic-fluid-conducting component of a vehicle for the purposes of examining oil and/or fuel and/or hydraulic fluid. By way of example, a pipe or a tube may be laid through a cylindrical receptacle of the measuring appliance, which completely pierces the measuring appliance and which coincides with the sensitive region of the nuclear magnetic resonance sensor. In this manner, the pipe or the tube is simultaneously secured against slipping in the measuring appliance. Furthermore, the nuclear magnetic resonance sensor may also be directly integrated at or in the motor, at an attached unit of the motor or in the oil dipstick, and thus facilitate an examination of the oil and/or fuel and/or a hydraulic fluid immediately at the usage location.

By using the measuring appliance specifically tailored to the application of examining oil and/or fuel and/or hydraulic fluid, it is possible to realize a precise and comprehensive examination of a fuel and/or oil and/or a hydraulic fluid in situ, for example in a workshop, in a warehouse, in a shop in a mobile manner, but also in a stationary manner in a motor compartment or the like, in a quick and non-destructive manner, and hence in a particularly cost-effective manner from an economical point of view. Advantageously, the use according to the disclosure of the measuring appliance facilitates the quick and precise examination of oil and/or fuel and/or hydraulic fluid at any location, i.e., in particular, independently of a laboratory specialized in nuclear magnetic resonance spectroscopy.

In one configuration, the measuring appliance is used for examining a fuel and/or oil and/or a hydraulic fluid, wherein the measurement signal supplied by the nuclear magnetic resonance sensor, in particular a spectrum and/or a relaxation time of the measurement signal resulting from the excitation of nuclear spins in the oil and/or fuel to be examined and/or in the hydraulic fluid to be examined by way of the nuclear magnetic resonance sensor, is evaluated by means of the evaluation apparatus of the measuring appliance.

According to the disclosure, the measuring appliance is used to comprehensively characterize an oil and/or a fuel and/or a hydraulic fluid, in particular in view of different features such as water distribution, water content, aging state, contaminants, composition, viscosity or the like. Here, spectra and relaxation times may be measured by means of the nuclear magnetic resonance sensor when using the measuring appliance, said spectra and/or relaxation times having a signature or characteristic dependent on the examined oil and/or fuel and/or hydraulic fluid, more precisely a signature or characteristic dependent on the atomic structure thereof. The evaluation apparatus is specifically embodied for a quick evaluation of the measurement signals supplied by the nuclear magnetic resonance sensor. In particular, quick means within 10 minutes, preferably within 60 seconds, particularly preferably within 5 seconds.

In the case of a suitable selection of the operating parameters of the nuclear magnetic resonance sensor, properties of the fuel and/or oil to be examined and/or the hydraulic fluid to be examined may be deduced directly by means of a spectrum and/or relaxation times of the response signal. By way of example, in the case of a chemometrics approach, there may be an examination of the fuel and/or oil and/or the hydraulic fluid, for example by an evaluation by means of principal component analysis (PCA), without knowing specific cause-effect relationships. Here, the spectrum or a plurality of spectra, chemical shifts, coupling constants, correlations and/or relaxation times or the like are used as input data for the evaluation. As a consequence of the evaluation, point clouds or graphically displayable regions are obtained, which may be evaluated further and, in particular, interpreted in a simple and quick manner by way of a comparison with reference data. By way of example, in one usage form of the measuring appliance, at least one information item from a list of information items may be evaluated by means of the evaluation apparatus from the measurement signals obtained from the nuclear magnetic resonance sensor, the list comprising at least

- a relative and/or absolute hydrocarbon content,
- bonding states of chemical compounds,
- a concentration gradient of a material and/or of a compound and/or of an element into the oil and/or into the fuel and/or into the hydraulic fluid,
- time-dynamic processes of chemical compounds in the oil and/or in the fuel and/or in the hydraulic fluid,
- a relative and/or absolute moisture content and/or
- further physically/chemically relevant parameters of the fuel and/or of the oil and/or of the hydraulic fluid.

Statements about the bonding states in the oil and/or fuel and/or in the hydraulic fluid render it possible to determine the material or constituent of the oil and/or of the fuel and/or of the hydraulic fluid. By way of example, this renders it possible to detect and distinguish different constituents, contaminants, inclusions or the like. It is likewise possible to realize a determination of a material concentration in the examined oil and/or fuel and/or in the hydraulic fluid to be examined provided there is a calibration of the nuclear magnetic resonance sensor prior to the measurement. In one embodiment, this material concentration may be compared to an admissible limit value (threshold) and a warning may be output by the measuring appliance if the threshold is exceeded.

By recording and evaluating time-dynamic processes of chemical compounds, it is possible to examine processes such as diffusion of moisture and/or decomposition in an oil and/or fuel and/or in a hydraulic fluid. Deductions in relation to possible aging of the fuel and/or of the oil and/or of the hydraulic fluid may be derived therefrom. Moreover, the measuring appliance may likewise be used to comprehensively characterize an oil and/or fuel and/or a hydraulic fluid in respect of moisture, for example to facilitate statements about the relative and/or absolute moisture content and about the moisture gradient into the oil and/or into the fuel and/or into the hydraulic fluid.

Further physically and/or chemically relevant parameters which may be evaluated using the measuring appliance with the evaluation apparatus comprise, in particular, a density, a porosity, a viscosity or the like of the examined fuel and/or oil and/or of the examined hydraulic fluid.

Depending on the desired information, the nuclear magnetic resonance sensor measures a spectrum and/or relaxation curves and/or relaxation times, wherein the evaluation apparatus carries out the targeted evaluation of these measurement signals in respect of the desired information.

In one configuration, the measuring appliance is used for examining a fuel and/or oil and/or hydraulic fluid, wherein ascertained information, in particular a spectrum and/or a relaxation time, is compared with reference data from a reference database by means of the evaluation apparatus of the measuring appliance.

In this way, there may be a particularly simple and comprehensive evaluation and/or assessment and/or interpretation of a measured measurement signal from the nuclear magnetic resonance sensor. By way of example, a recorded spectrum and/or recorded relaxation curves, in particular relaxation times, may be compared with reference spectra, reference relaxation curves or reference relaxation times. The comparison of the measurement signals with known reference data which were determined in detail in this case serves for the quick and simple assignment of the measurement signal in order to derive specific information from the measured measurement signal. By way of the comparison with known reference data, it is furthermore possible—in addition to a very high evaluation speed—to obtain a particularly accurate result, i.e. particularly accurate information about the examined oil and/or the examined fuel and/or the examined hydraulic fluid. By way of example, a shift in a measured spectrum may be identified very easily and quickly in a comparison with a reference spectrum, and so information relating to the examined oil and/or the fuel and/or the examined hydraulic fluid is derivable from this shift.

Advantageously, deviations of the measurement signals from the reference data may be identified in a particularly simple manner by comparing the measured measurement signals with reference data. If these deviations exceed a defined tolerance threshold, they may be interpreted as an indication for irregularity and/or discrepancies in relation to the examined oil and/or the examined fuel and/or the examined hydraulic fluid.

The reference data, in particular reference curves and/or reference values and/or reference spectra, may in this case be stored within the appliance in a database in a memory unit, in particular a memory unit of the control and/or evaluation apparatus. In an alternative or additional embodiment, the reference data may also be stored in a reference database which is external to the appliance and advantageously always up-to-date, for example in a reference database in a computer, a server or a different data memory and/or data processing appliance appearing expedient to a person skilled in the art. In particular, the comparison between the measured measurement signals and the reference data may be carried out by way of an Internet access of the measuring appliance. Alternatively, or additionally, reference data stored within the appliance may likewise be updated by way of an Internet access of the measuring appliance, for example by comparison with a reference database which is external to the appliance.

In one configuration, the measuring appliance is used for examining a fuel and/or oil and/or a hydraulic fluid, wherein ascertained information, in particular a spectrum and/or a relaxation time, and/or a deviation of ascertained information from reference data from a reference database is output, in particular displayed, by means of the output apparatus of the measuring appliance, in particular by means of a display.

Using the information output, in particular displayed, by means of the output apparatus, it is possible, in particular for an operator of the measuring appliance, to obtain a result after carrying out the examination of the fuel and/or oil and/or the hydraulic fluid.

In one embodiment, the information relating to the examined oil and/or the examined fuel is output to the operator of the measuring appliance by means of a display of the output apparatus in an intuitively understandable, in particular prepared, manner. In particular, the output is intuitive if the operator is able to carry out an examination of a fuel and/or an oil and/or a hydraulic fluid and subsequently able to derive a statement, preferably an assessment, from the depicted information without prior knowledge. In one embodiment, a preparation of the ascertained information may be carried out e.g. in the form of a color assignment. By way of example, red may, in this case, signal an ascertained critical deviation of an examined target variable—e.g. quality—from a prescription—e.g. defined by the reference data in the reference database. By contrast, yellow signals a deviation within an admissible tolerance and green signals an ascertained deviation with an admissible and/or harmless effect. Alternatively, or additionally, an output of the ascertained information may be effected in the form of a short message, which is depicted on the display. By way of example, this short message may contain a specification of the reference data used to evaluate the examined fuel and/or oil and/or the hydraulic fluid, further an assessment of the deviation, to the extent that it is ascertained, and recommendations derived therefrom, such as "oil aged, replacement recommended" or "density and viscosity correspond to manufacturer specifications" or the like.

In an alternative or additional configuration, the measuring appliance is used for examining a fuel and/or oil and/or a hydraulic fluid, wherein ascertained information, in particular a spectrum and/or a relaxation time, and/or a deviation of ascertained information from reference data in a reference database, is output, in particular displayed, at and/or in an operator's platform. In this manner, information ascertained by means of a measuring appliance integrated into a vehicle may be output to the vehicle driver during operation of the vehicle.

In one configuration, the measuring appliance is used for examining a fuel and/or oil and/or a hydraulic fluid, wherein ascertained information is used for open-loop and/or closed-loop control of at least one component of the vehicle. In this embodiment, the information relating to the examined oil and/or the examined fuel and/or the examined hydraulic fluid is forwarded to a further external appliance, in particular to a component of a vehicle, for example a motor controller, a brake booster controller or the like. In this way, the information serves for improved, in particular optimized, open-loop and/or closed-loop control of the external appliance or of the component of the vehicle or of the system under open-loop and/or closed-loop control by means of the external appliance or the component of the vehicle—for example of a motor. In a specific exemplary embodiment, it is possible, in particular, to determine, using the measuring appliance, a density, porosity, viscosity, a water content and a gas content of a brake fluid of a motor vehicle continuously or at regular intervals during the operation of the motor vehicle. The information ascertained thus is subsequently forwarded to a brake booster controller of the motor vehicle and used thereby for optimized open-loop and/or closed-loop control of the braking force. By way of example, this allows selection of a stronger brake power during a braking process in the case of a relatively high gas content in the brake fluid, said braking power compensating the compressibility of the gas contained in the brake fluid.

In one configuration, the measuring appliance is used for examining a fuel and/or oil and/or a hydraulic fluid, wherein specifications relating to an oil and/or fuel and/or a hydraulic fluid are specified by operator inputs by means of an input apparatus and made available to the measuring appliance.

In particular, an input apparatus should be understood to be a means provided to receive at least one information item from an operator of the measuring appliance by way of an acoustic, optical, gesture-supported and/or tactile input and forward this to the control apparatus of the measuring appliance. By way of example, the input apparatus may consist of an actuating element, a keyboard, a display, in particular a touch-display, a speech input module, a gesture recognition unit and/or a pointer appliance (e.g. a mouse).

Alternatively, or additionally, the input apparatus may also be realized outside of the measuring appliance, for example in the form of an external data processing appliance such as a smartphone, a tablet PC, a PC or an onboard computer of a vehicle or the like, which is connected to the control apparatus of the measuring appliance by way of a data communication interface.

By entering specifications in relation to an oil and/or fuel and/or a hydraulic fluid, it is possible to advantageously adapt information processing, in particular the evaluation of the measurement signal, the comparison of a measurement signal and/or ascertained information with reference data or the like, to the oil to be examined and/or the fuel and/or the hydraulic fluid. By way of example, a reference database may be selected depending on an operator input. Furthermore, it is possible to adapt an operating program of the control apparatus, closed-loop control routines, open-loop control routines, evaluation routines and/or calculation routines, particularly in conjunction with the specification.

By way of example, "specifications in relation to an oil and/or fuel and/or a hydraulic fluid" may characterize the oil and/or the fuel and/or the hydraulic fluid itself ("diesel", "petrol", "biodiesel", "brake fluid") and/or relate to a producer. Alternatively, or additionally, specifications, in particular further specifications relating to the physical and/or chemical properties of the fuel and/or oil and/or the hydraulic fluid, may be expedient and/or necessary.

In one configuration, the measuring appliance is used for examining a fuel and/or oil and/or a hydraulic fluid, wherein the measuring appliance is calibrated using a standard sample provided within the appliance, in particular using a tetramethylsilane sample provided within the to appliance, before examining a fuel and/or oil and/or a hydraulic fluid.

Therefore, for the purposes of examining a fuel and/or oil and/or a hydraulic fluid in more detail, there may be a calibration of the measuring appliance, in particular a calibration of the nuclear magnetic resonance sensor, prior to carrying out the examination. In one embodiment, the calibration is carried out using a pure material sample, preferably using a tetramethylsilane (TMS) sample, provided in particular within the appliance, which is used as a standard. All measurements following the calibration, in particular measurements of an oil and/or fuel to be examined and/or a hydraulic fluid to be examined, are evaluated in relation to this calibration measurement.

Furthermore, a measuring appliance according to the disclosure, in particular a hand-held measuring appliance, preferably a measuring appliance comprising a housing, for examining oil and/or fuel and/or hydraulic fluid is proposed, comprising at least a nuclear magnetic resonance sensor, a control apparatus for controlling the measuring appliance, an evaluation apparatus for evaluating a measurement signal supplied by the nuclear magnetic resonance sensor, an output apparatus for outputting ascertained information, and an apparatus for energy supply, wherein the measuring appliance, in particular the nuclear magnetic resonance sensor and/or the evaluation apparatus, is provided for examining fuel and/or oil and/or hydraulic fluid.

Naturally, the already made descriptions in respect of the use of the measuring appliance, in particular the explanations in respect of the evaluation apparatus and the nuclear magnetic resonance sensor, also apply accordingly to the measuring appliance itself.

In one embodiment of the measuring appliance, provision is further made of a memory apparatus for storing measurement results and/or working parameters. This memory apparatus may comprise all forms of external and internal electronic memories, in particular digital memories, in particular also memory chips such as USB sticks, memory sticks, memory cards, etc.

Moreover, what is proposed is that the control apparatus and/or the evaluation apparatus of the measuring appliance according to the disclosure comprises a data communication interface for communication, in particular wireless communication, purposes, by means of which the measuring appliance may transmit and/or receive measurement results and/or working parameters. Preferably, the data communication interface uses a standardized communication protocol for transferring electronic data, in particular digital data. Advantageously, the data communication interface comprises a wireless interface, in particular e.g. a WLAN interface, Bluetooth interface, infrared interface, NFC interface, RFID interface, GSM interface or any other wireless interface appearing expedient to a person skilled in the art. Alternatively, the data communication interface may also comprise a wired adapter, for example a USB adapter or micro-USB adapter. Advantageously, measurement results and/or working parameters may, by way of the data communication interface, be transmitted from the measuring appliance to an external data appliance, for example to a smartphone, a tablet PC, a PC, a printer or further external appliances appearing expedient to a person skilled in the art, or said measurement results and/or working parameters may be received by the latter. Advantageously, a transfer of reference data which is usable for further evaluation of measurement signals captured by the measuring appliance may be facilitated by means of the configuration according to the disclosure. In particular, the reference data are in this case recalled from an appliance-internal reference database. Furthermore, multifaceted additional functions may advantageously be facilitated and included, said additional functions, in particular, also requiring direct communication with smartphones (in particular by way of programmed apps) or similar portable data appliances. By way of example, these may comprise automatic mapping functions, firmware updates, data post-processing, data preparation, data comparison with other appliances, etc.

Furthermore, a method according to the disclosure for examining oil and/or fuel and/or hydraulic fluid by means of a measuring appliance, in particular a hand-held measuring appliance, is proposed. In a preferred embodiment of the method, the method may, in particular, be characterized by at least the following steps:
  i. calibrating the nuclear magnetic resonance sensor using a standard sample, in particular using a tetramethylsilane sample provided within the appliance
  ii. measuring at least one spectrum and/or one relaxation time resulting from the excitation of nuclear spins in the oil to be examined and/or in the fuel to be examined and/or in the hydraulic fluid to be examined
  iii. evaluating measurement signals from the nuclear magnetic resonance sensor by comparing the measurement signals with reference data from a reference database
  iv. outputting the evaluation results, in particular ascertained information and/or a deviation of ascertained information from reference data of a reference database.

BRIEF DESCRIPTION OF THE DRAWINGS

The disclosure is explained in more detail in the subsequent description on the basis of exemplary embodiments depicted in the drawings. The drawing, the description and the claims contain numerous features in combination. Expediently, a person skilled in the art will also consider the features on their own and combine these to give further meaningful combinations. In the figures, the same or similar reference signs denote the same or similar elements.

In detail.

DETAILED DESCRIPTION

Figure 1:
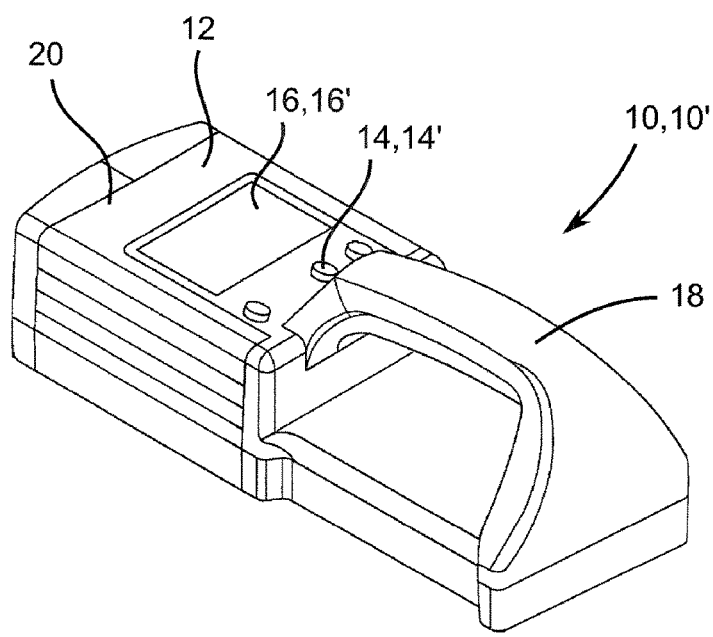
FIG. 1 shows a perspective illustration of a configuration of the measuring appliance according to the disclosure.
Figure 2:
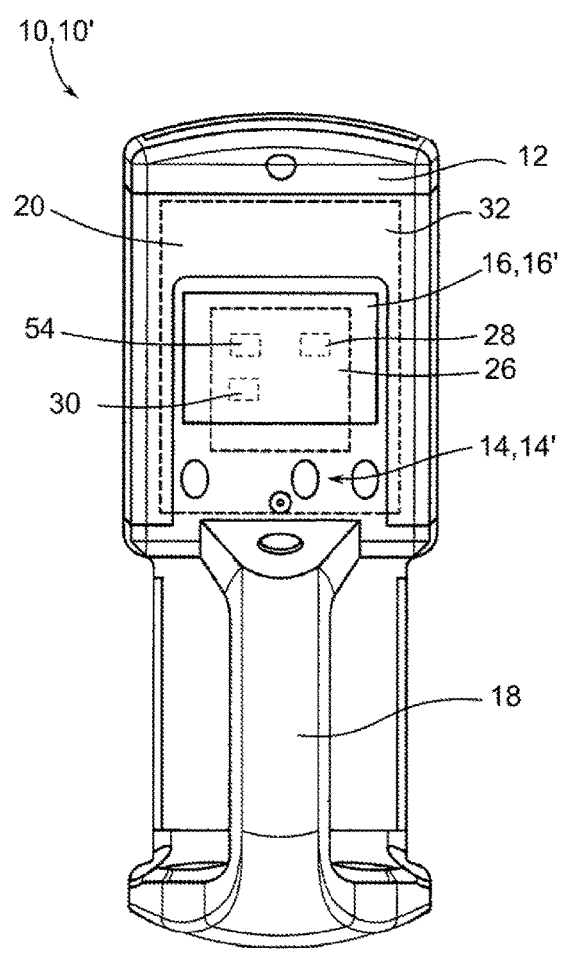
FIG. 2 shows a view of the first housing side of a configuration of the measuring appliance according to the disclosure.

FIG. 1 and FIG. 2 show two views of an exemplary embodiment of the measuring appliance 10 according to the disclosure, in a perspective illustration and in a simplified, schematic plan view. The measuring appliance 10 is realized as a hand-held, energy-independent measuring appliance 10' in the depicted embodiment.

The measuring appliance 10' embodied in an exemplary manner comprises a housing 12. The housing 12 houses an input apparatus 14 in the form of actuation elements 14', suitable for switching the measuring appliance 10' on and off, starting and configuring a measurement process and entering working parameters. Furthermore, an output apparatus 16 for outputting ascertained information and for outputting working parameters in the form of a display 16' is provided in the housing 12. For transportation purposes and for the guidance thereof, the measuring appliance 10' comprises a handle 18. The handle 18, the actuation elements 14' and the display 16' are situated on a first housing side 20 of the measuring appliance 10 (also referred to as "front side"), which typically faces the operator when the measuring appliance is operated.

For the purposes of supplying the measuring appliance 10' with energy, the measuring appliance 10' has a recess on the second housing side 40 (also referred to as rear side of the measuring appliance below) lying opposite to the first housing side 20 on the rear side of the appliance, said recess serving to receive power-grid-independent energy stores 22 in the form of rechargeable accumulators (cf. FIG. 3). On account of the power-grid-independent energy store 22, the measuring appliance 10' may be operated, at least temporarily, in an energy-independent manner, i.e. independently of a power grid and hence, in particular, without cables as well. The measuring appliance 10' presented in an exemplary manner comprises lithium ion accumulators, the high energy density and power density of which is advantageously suitable for supplying the measuring appliance 10' with energy. In an alternative embodiment, the energy store 22 may also be housed in the handle 18 of the measuring appliance 10'. Preferably, the apparatus for energy supply comprises a detachable interlocking and/or force-fit connection interface such that the energy store 22 (in general, also a plurality of energy stores) is (are) arrangeable in a removable and interchangeable manner. Moreover, the energy store 22 may be supplied with energy from a power grid and may be charged within and/or outside of the measuring appliance.

Figure 3:
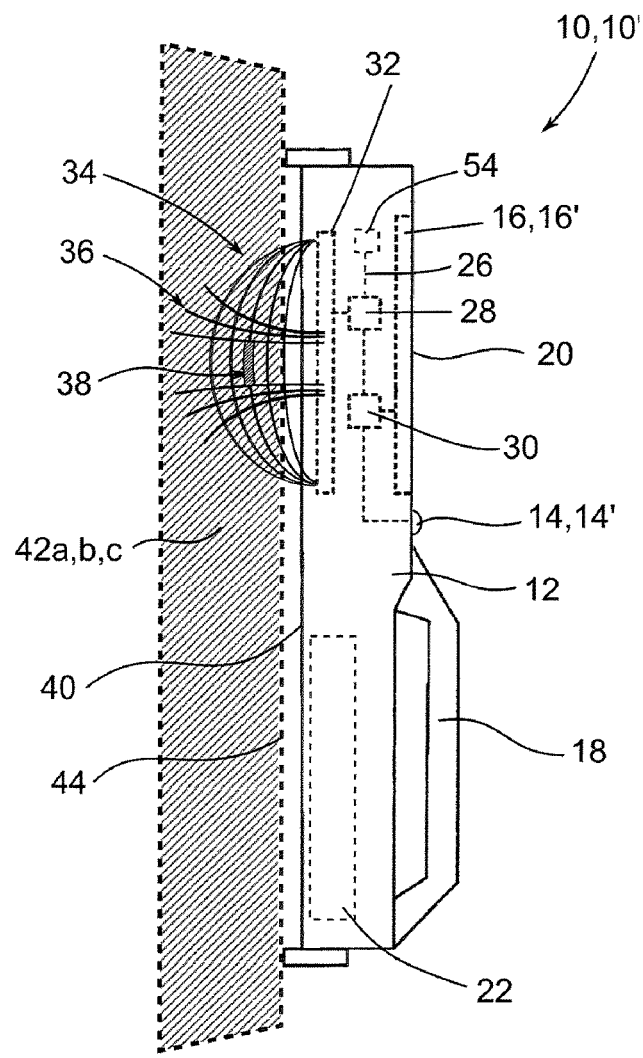
FIG. 3 shows a schematic side view of a configuration of the measuring appliance according to the disclosure.

Further components of the measuring appliance 10', in particular a nuclear magnetic resonance sensor 32, a control apparatus 28 for controlling the measuring appliance 10', an evaluation apparatus 30 for evaluating measurement signals supplied by the nuclear magnetic resonance sensor 32 and a data communication interface 54 connected to the control and/or evaluation apparatus, are housed on a carrier element 26, in particular on a system circuit board or printed circuit board within the housing 12 (see, in particular, FIGS. 2 and 3).

Figure 4A:
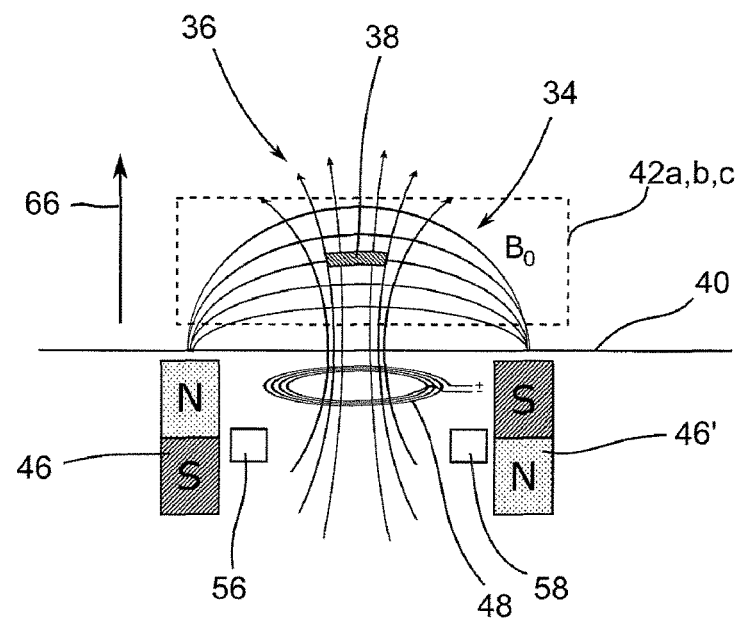
FIG. 4a shows a schematic sectional illustration of an embodiment of the components forming the nuclear magnetic resonance sensor and the magnetic fields generated thereby.
Figure 4B:
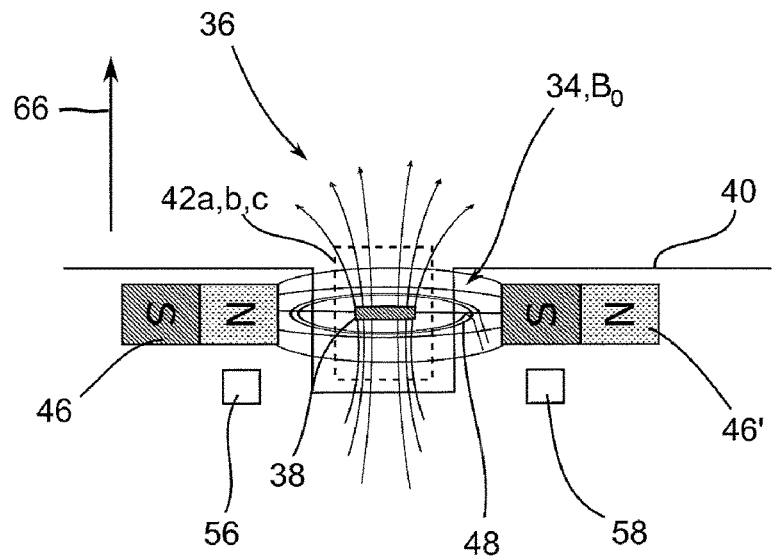
FIG. 4b shows a schematic sectional illustration of an alternative embodiment of the components forming the nuclear magnetic resonance sensor and the magnetic fields generated thereby.

The nuclear magnetic resonance sensor 32, which is explained in detail in the description relating to FIGS. 4a and 4b, is provided to excite a nuclear magnetic resonance in atomic nuclei of the material of the fuel 42a and/or oil 42b and/or the hydraulic fluid 42c. According to the disclosure, the measured resonance signal, in particular a spectrum, relaxation curves and/or relaxation times, is used at least for the non-destructive and contamination-free examination of the fuel 42a and/or oil 42b and/or the hydraulic fluid 42c. In this way, it is possible to ascertain information which, inter alia, relates to the quality, age, purity, composition, viscosity or the like of the fuel 42a and/or of the oil 42b and/or of the hydraulic fluid 42c.

The control apparatus 28 has control electronics comprising means for communicating with the other components of the measuring appliance 10', for example means for open-loop and closed-loop control of the nuclear magnetic resonance sensor 32, of the evaluation apparatus 30 and the like. In particular, the control apparatus 28 comprises a unit with a processor unit, a memory unit and an operating program stored in the memory unit. The control apparatus 28 is provided to adjust at least one operating functional parameter of the measuring appliance 10' depending on at least one input by the operator, via the evaluation apparatus 30 and/or via the data communication interface 54.

The evaluation apparatus 30 for evaluating measurement signals supplied by the nuclear magnetic resonance sensor 32 comprises, in particular, an information input, an information processing element and an information output (not depicted in any more detail). Advantageously, the evaluation apparatus 30 consists of at least a processor and a memory with an executable operating program stored thereon, and renders it possible to evaluate at least one measurement signal from the nuclear magnetic resonance sensor 32 and hence determine information relating to the quality, age, purity, composition or the like of the fuel 42a and/or oil 42b and/or of the hydraulic fluid 42c. Furthermore, the evaluation apparatus 30 has stored correction and/or calibration tables which render it possible to interpret, convert, interpolate and/or extrapolate the evaluation results and calibrate the measuring appliance 10', in particular the evaluation routines, in respect of a fuel 42a and/or oil 42b and/or a hydraulic fluid 42c. The evaluation results are output for further use by the evaluation apparatus 30 via the control apparatus 28, either directly to an operator of the measuring appliance 10' or to the data communication interface 54 for the purposes of data transmission. In particular, the evaluation results and/or measurement results may be compared with reference data stored in a reference database using the data communication interface 54.

FIG. 3 depicts an embodiment of a measuring appliance 10', in particular of the hand-held measuring appliance 10' from FIGS. 1 and 2, in a simplified schematic side view. The nuclear magnetic resonance sensor 32 comprises two apparatuses for generating magnetic fields, in particular a permanent magnet arrangement 46, 46' (cf. FIGS. 4a, 4b, but also FIGS. 5b, 5c) which generates a first magnetic field 34 ($B_0$) and a radiofrequency coil 48 (cf. FIGS. 4a, 4b, 5b, 5c) which generates a second magnetic field 36. The nuclear magnetic resonance sensor 32 is configured in such a way that the first magnetic field 34 (represented by magnetic field lines in the figures) is aligned substantially parallel to the second housing side 40 while the second magnetic field 36 is aligned substantially perpendicular to the magnetic field lines of the first magnetic field 34. The two magnetic fields superpose in an extended region, in which the sensitive region 38 of the nuclear magnetic resonance sensor 32 is situated, in particular as a layer-shaped region. The hand-held measuring appliance 10' is positioned with the second housing side 40 in the direct vicinity of a fuel 42a to be examined and/or of an oil 42b to be examined and/or of a hydraulic fluid 42c to be examined, in such a way that the distance between the second housing side 40 and the surface 44 of the fuel 42a and/or oil 42b and/or the hydraulic fluid 42c (liquid surface or else, alternatively, container surface) is minimized. What this achieves is that the magnetic fields 34, 36 penetrate into the oil 42b and/or into the fuel 42a and/or into the hydraulic fluid 42c and the sensitive region 38 comes to rest in the oil 42b and/or in the fuel 42a and/or in the hydraulic fluid 42c.

By varying the second magnetic field 36 generated by the second device, i.e., in particular, by varying the radiofrequency coil 48 and/or varying the frequency and/or varying the current and/or varying the voltage in the radiofrequency coil 48, it is possible to vary the sensitive region 38 in terms of its distance from the second housing side 40 (in the direction 66 (cf. FIGS. 4a, 4b, 5b, 5c) into the oil 42b and/or into the fuel 42a and/or into the hydraulic fluid 42c) and hence modify the distance of the sensitive region 38 in the oil 42b and/or in the fuel 42a and/or in the hydraulic fluid 42c. Alternatively, and/or additionally, the nuclear magnetic resonance sensor 32 may be repositioned in the housing 12 of the measuring appliance 10' in such a way that the distance between the nuclear magnetic resonance sensor 32 and the second housing side 40 is varied and consequently the distance of the sensitive region 38 in the oil 42a and/or in the fuel 42a and/or in the hydraulic fluid 42c from the surface 44 of the latter is also varied. Depth profiles of the information to be evaluated may be created particularly advantageously in this manner. By way of example, it is possible to make a statement about the progress of an aging process by way of a depth profile of a moisture curve in an oil 42b and/or fuel 42 42a.

FIG. 4a depicts the nuclear magnetic resonance sensor 32 together with an oil 42b and/or fuel 42a to be examined and/or a hydraulic fluid 42c to be examined in a schematic sectional illustration of a detail of an exemplary embodiment of a measuring appliance 10, in particular of the hand-held measuring appliance 10'. Two permanent magnets 46, 46' which are arranged perpendicular to the second housing side 40 of the measuring appliance 10' and antiparallel in relation to one another generate a first magnetic field 34, in particular a static magnetic field, which extends substantially parallel to the surface of the second housing side 40. This first magnetic field 34 provided for aligning the nuclear spins of the atomic nuclei present in the oil 42b and/or in the fuel 42a and/or in the hydraulic fluid 42c has, for example, in particular, a magnetic field strength of 0.5 Tesla, with the permanent magnets 46, 46' being produced from a neodymium iron boron alloy. In an alternative embodiment, the magnetic field 34 may also be generated by means of an electromagnet. In this exemplary embodiment, the second apparatus for generating the second magnetic field is formed by a radiofrequency coil 48. As soon as current flows through this coil, an electromagnetic field, in particular the second magnetic field 36, is induced. The two magnetic fields 34, 36 superpose in a region which lies substantially outside of the housing 12 of the measuring appliance 10'. The sensitive region 38 of the nuclear magnetic resonance sensor 32 likewise lies in the superposition field of the magnetic fields 34 and 36. Depending on the frequency of the radiated electromagnetic field 36 and the static magnetic field strength of the first magnetic field 34, the sensitive region is defined by an area in an ideal case, in which the magnetic field strength of the first magnetic field 34 is constant and, in particular, has a defined magnitude. In reality, the area in fact has a layered shape on account of non-exact frequencies. Since the magnetic field lines 34 do not extend exactly parallel to the second housing side 40, the sensitive region 38 is therefore also curved in a manner corresponding to the magnetic field lines as a consequence thereof. The curvature and form of the first magnetic field 34, and hence of the sensitive region 38, may be influenced and, in particular, homogenized using further means, for example a shim coil 56 and a magnetic shield 58.

The surface 40 of the housing 12 of the measuring appliance 10' represents a plane surface in this exemplary embodiment, on which the oil 42b to be examined and/or the fuel 42a and/or the hydraulic fluid 42c to be examined may be placed.

FIG. 4b depicts the nuclear magnetic resonance sensor 32 together with an oil 42b and/or fuel 42a to be examined and/or a hydraulic fluid 42c to be examined in a schematic sectional illustration of a detail of an alternative embodiment of a measuring appliance 10, in particular of the hand-held measuring appliance 10'. Here, the first magnetic field 34, in particular static magnetic field, generated by the first apparatus, in this case two parallel permanent magnets 46, 46' (with a North-South/North-South sequence) arranged parallel to the second housing side and collinearly, is arranged substantially parallel to the second housing side 40 of the measuring appliance 10'. The second magnetic field 36 generated by the second apparatus, in this case a radiofrequency coil 48, is aligned substantially perpendicular to the first magnetic field 34. In an alternative embodiment, the magnetic field 34 may also be generated by means of an electromagnet. The radiofrequency coil 48, the winding plane of which lies collinearly with the direction of extent of the permanent magnets 46, 46' and parallel to the second housing side 40, lies between the two permanent magnets 46, 46'. This arrangement is positioned in the direct vicinity of the second housing side 40 in the interior of the measuring appliance 10'. As soon as current flows through this coil, an electromagnetic field, in particular the second magnetic field 36, is induced. The two magnetic fields superpose in a region which lies substantially outside of the housing 12 of the measuring appliance 10'. The sensitive region 38 of the nuclear magnetic resonance sensor 32 likewise lies in the superposition field of the magnetic fields 34 and 36. Depending on the frequency of the radiated electromagnetic field 36 and the static magnetic field strength of the first magnetic field 34, the sensitive region is defined by an area in an ideal case, in which the magnetic field strength of the first magnetic field 34 is constant and, in particular, has a defined magnitude. In reality, the area in fact has a layered shape on account of non-exact frequencies. Since the magnetic field lines 34 do not extend exactly parallel to the second housing side 40, the sensitive region 38 is therefore also curved in a manner corresponding to the magnetic field lines as a consequence thereof. The curvature and form of the first magnetic field 34, and hence of the sensitive region 38, may be influenced and, in particular, homogenized using further means, for example a shim coil 56 and a magnetic shield 58.

In this exemplary embodiment, the surface 40 of the housing 12 of the measuring appliance 10' does not constitute a plane surface, but has a receptacle 50 formed specifically for receiving a fuel 42a and/or oil 42b to be examined and/or a hydraulic fluid 42c to be examined. The receptacle 50 and the arrangement of the nuclear magnetic resonance sensor 32 are matched to one another in such a way that the oil 42b and/or the fuel 42a and/or the hydraulic fluid 42c, for example situated in a container, is introduced into the receptacle 50. Here, the sensitive region 38 of the nuclear magnetic resonance sensor 32 comes immediately to rest in the oil 42b and/or in the fuel 42a and/or in the hydraulic fluid 42c.

Figure 5A:
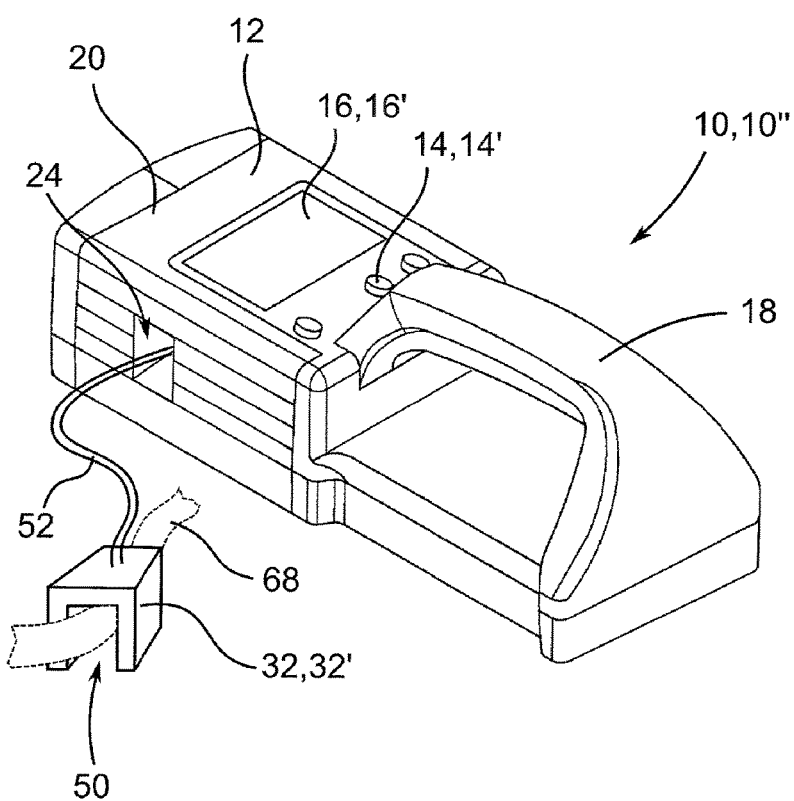
FIG. 5a shows a perspective illustration of an alternative configuration of the measuring appliance according to the disclosure.

FIG. 5a shows an alternative or additional exemplary embodiment of a measuring appliance 10 according to the disclosure in a perspective illustration. The depicted measuring appliance 10" in this exemplary embodiment may be used as a hand-held, energy-independent measuring appliance and be able to be integrated into a motor compartment of a motor vehicle. In particular, the statements made in relation to the exemplary embodiments in FIGS. 1 to 4b also apply figuratively to this exemplary embodiment.

Compared to the measuring appliance 10' depicted in FIG. 1, the measuring appliance 10" comprises a nuclear magnetic resonance sensor 32 which is housed in a small measuring head 32' which is connected to the measuring appliance 10' by way of a cable 52. For the purposes of transporting the measuring appliance 10', the measuring head 32' may be stored in a recess 24 in the housing 12 of the measuring appliance 10'. The measuring head 32' has a C-shaped receptacle 50, by means of which the measuring head 32' may be placed onto a fuel-conducting and/or oil-conducting and/or hydraulic-fluid-conducting component of a motor vehicle and fastened there. In FIG. 5a, the measuring head 32' is fastened in an exemplary manner to a tube 68, for example a brake hose.

Figure 5B:
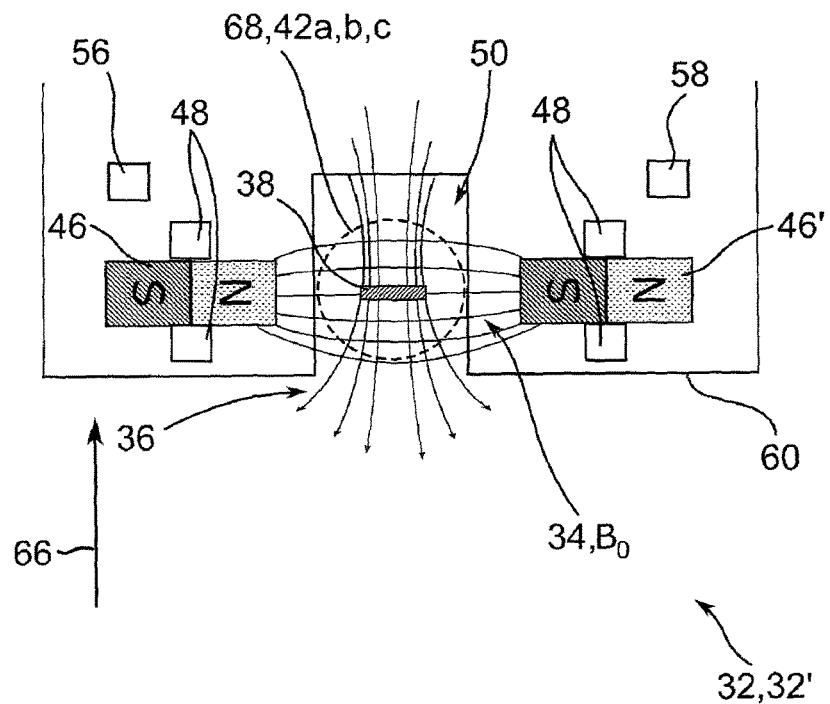
FIG. 5b shows a schematic sectional illustration of an alternative embodiment of the components forming the nuclear magnetic resonance sensor and the magnetic fields generated thereby.

FIG. 5b depicts the nuclear magnetic resonance sensor 32 together with an oil 42b and/or fuel 42a to be examined and/or a hydraulic fluid 42*c* to be examined—in this case e.g. a brake fluid to be examined—in a schematic sectional illustration of an exemplary embodiment of the measuring head 32', said substance to be examined being situated in the tube 68. The measuring head 32' has a substantially C-shaped form with a receptacle 50 that is open on two opposite sides. In this manner, the receptacle 50 of the measuring head 32' may be positioned on the tube 68 and fixed by means of fixation elements (not depicted in any more detail here) in such a way that the tube 68 extends along the direction provided by the two open sides of the receptacle 50.

Two collinearly arranged permanent magnets 46, 46', aligned in a North-South/North-South sequence, generate a first magnetic field 34, in particular a static magnetic field, which passes through the receptacle 50 in a substantially homogeneous manner. This first magnetic field 34 provided for aligning the nuclear spins of the atomic nuclei present in the oil 42*b* to be examined and/or fuel 42*a* and/or in the hydraulic fluid 42*c* to be examined has, for example, in particular a magnetic field strength of 0.5 Tesla, with the permanent magnets 46, 46' being produced from a neodymium iron boron alloy in this exemplary embodiment. In an alternative embodiment, the magnetic field 34 may also be generated by means of an electromagnet. In this exemplary embodiment, the second apparatus for generating the second magnetic field is formed by a radiofrequency coil 48 in the form of a space-saving saddle coil. As soon as current flows through this coil, an electromagnetic field, in particular the second magnetic field 36, is induced. The second magnetic field 36 generated by the radiofrequency coil 48 is aligned substantially perpendicular to the first magnetic field 34, with the two magnetic fields 34, 36 in a region, which lies substantially outside of the housing 12, in particular outside of the housing surface 60 of the measuring head 32', of the measuring head 32', but within the receptacle 50 of the measuring head 32'. The sensitive region 38 of the nuclear magnetic resonance sensor 32 likewise lies in the superposition field of the magnetic fields 34 and 36, and hence within the receptacle 50, outside of the surface 66 of the measuring head 32'. Depending on the frequency of the radiated electromagnetic field 36 and the static magnetic field strength of the first magnetic field 34, the sensitive region is defined by an area in an ideal case, in which the magnetic field strength of the first magnetic field 34 is constant and, in particular, has a defined magnitude. In reality, the area in fact has a layered shape on account of non-exact frequencies. Since the magnetic field lines 34 do not extend exactly parallel, the sensitive region 38 is therefore also curved in a manner corresponding to the magnetic field lines as a consequence thereof. The curvature and form of the first magnetic field 34, and hence of the sensitive region 38, may be influenced and, in particular, homogenized using further means, for example a shim coil 56 and a magnetic shield 58.

Figure 5C:
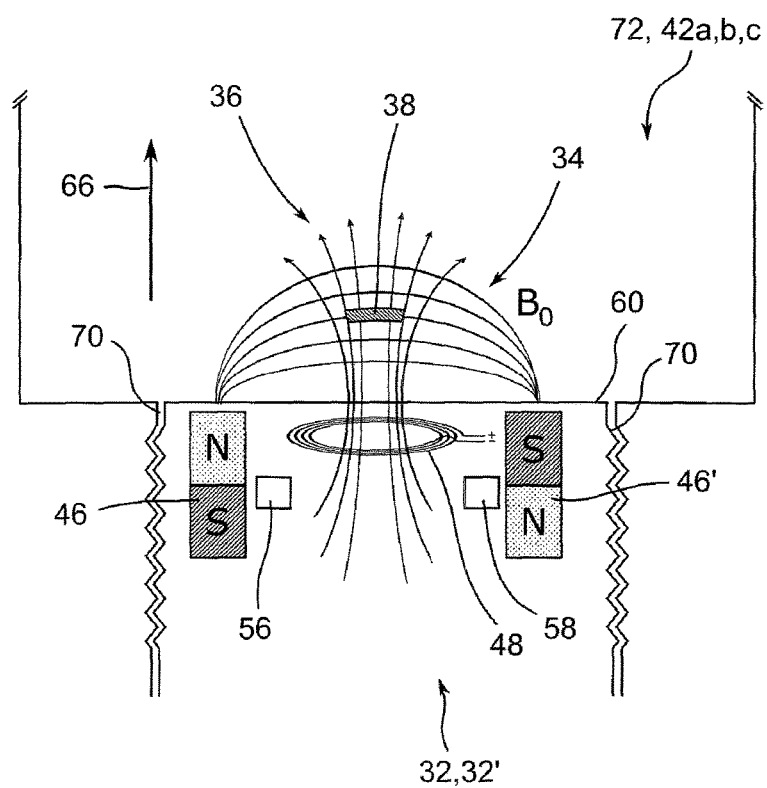
FIG. 5c shows a schematic sectional illustration of an alternative embodiment of the components forming the nuclear magnetic resonance sensor and the magnetic fields generated thereby.

Furthermore, it is conceivable for the nuclear magnetic resonance sensor 32 to be integrated directly at or in a motor, at an attached unit of a motor, in an oil dipstick or in an oil-conducting and/or fuel-conducting and/or hydraulic-fluid-conducting pipe or tube. By way of example, the measuring head 32' of the nuclear magnetic resonance sensor 32 may be embodied with a thread 70, wherein the thread 70 may be used to realize fixation in the oil-conducting and/or fuel-conducting and/or hydraulic-fluid-conducting component 72 of a vehicle. In this way, the magnetic fields 34, 36 generated by the nuclear magnetic resonance sensor 32 and, in particular, the sensitive region 38 come to rest in the oil 42*b* and/or fuel 42*a* and/or in the hydraulic fluid 42*c* of the oil-conducting and/or fuel-conducting and/or hydraulic-fluid-conducting component. FIG. 5*c* reproduces such an embodiment of the measuring head 32' in a further schematic sectional illustration.

The evaluation results ascertained by the measuring appliance 10' are output at least to an external appliance such as e.g. a motor control appliance or a brake booster controller for further use. The motor control appliance or the brake booster controller uses the ascertained information for open-loop and/or closed-loop control of the motor or of the braking force during a braking process of the vehicle, which control is adapted in relation to the actually present properties of the oil 42*b* and/or of the fuel 42*a* and/or of the hydraulic fluid 42*c* (in this case: brake fluid properties) and is therefore improved, preferably optimized.

Figure 6:
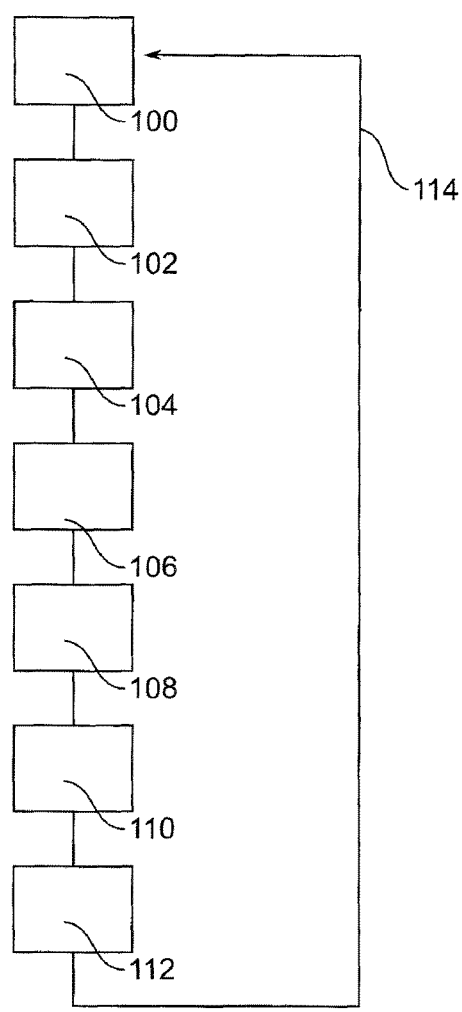
FIG. 6 shows a flowchart of an embodiment of the method according to the disclosure.

FIG. 6 shows a flowchart which represents an exemplary embodiment of the method according to the disclosure for examining oil 42*b* and/or fuel 42*a* and/or hydraulic fluid 42*c* by means of a measuring appliance 10, in particular by means of a hand-held measuring appliance 10'. In a first method step 100, the measuring appliance 10 is switched on and it is in an idle mode after a short startup time. Subsequently, specifications in relation to a fuel 42*a* to be examined and/or an oil 42*b* to be examined and/or a hydraulic fluid 42*c* to be examined are specified in an optional method step 102 using the input apparatus 14. In method step 104, there is a calibration of the nuclear magnetic resonance sensor 32 using a tetramethylsilane sample provided within the appliance, following which the measuring appliance 10 is ready for use for examining the fuel 42*a* and/or oil 42*b* and/or the hydraulic fluid 42*c*. For the purposes of measuring a nuclear magnetic resonance signal in the oil 42*b* and/or in the fuel 42*a* and/or in the hydraulic fluid 42*c*, the measuring appliance 10 is (optionally) positioned in a planar manner with the second housing side 40 thereof in the direct vicinity of the oil 42*b* and/or fuel 42*a* and/or the hydraulic fluid 42*c*, in particular in contact with the surface 44 thereof, in method step 106—in this case in an exemplary manner corresponding to the geometric embodiment of the measuring appliance 10 according to the exemplary embodiment from FIG. 4*a*. Here, the magnetic fields 34, 36 generated by the nuclear magnetic resonance sensor 32 penetrate out of the measuring appliance 10, through the second housing side 40 and into the oil 42*b* and/or into the fuel 42*a* and/or into the hydraulic fluid 42*c*, with the sensitive region 38 coming to rest in the oil 42*b* and/or in the fuel 42*a* and/or in the hydraulic fluid 42*c* (see, in particular, FIGS. 3, 4*a*, 4*b*, 5*b*, 5*c*). Magnetic field changes as a consequence of a nuclear magnetic resonance effect of the nuclear spins of the atomic nuclei excited in the oil 42*b* and/or fuel 42*a* and/or in the hydraulic fluid 42*c*, i.e. caused by absorption and/or emission of electromagnetic fields by the atomic nuclei, accompanied by a change in the energy states thereof, are detected by means of the radiofrequency coil 48 of the nuclear magnetic resonance sensor 32 (method step 108). This measurement signal, in particular a measurement signal representing a spectrum and/or relaxation curves, is forwarded to the evaluation apparatus 30, where it is prepared, in particular filtered and/or smoothed, by means of evaluation routines. Subsequently, the measurement signal from the nuclear magnetic resonance sensor is evaluated by comparing the measurement signal with reference data in a reference database (method step 110). In the process, the measured spectra and/or relaxation curves and/or relaxation times are compared to reference spectra or reference relaxation curves or reference relaxation times. Identifying correspondences, and/or deviations, of the measurement signal with, or from, the reference data allows the quick and precise evaluation of the measurement signal in this method step, in which information relating to the examined oil 42b and/or the examined fuel 42a and/or the examined hydraulic fluid 42c are obtained and prepared. The evaluation results, in particular the ascertained information and/or a deviation of the ascertained information from reference data in the reference database, are subsequently forwarded by means of to the output apparatus 16 (method step 112). The evaluated measurement result, i.e. the information relating to the examined oil 42b and/or the examined fuel 42a and/or the examined hydraulic fluid 42c, may be depicted to the operator of the measuring appliance 10 on the display 16' and/or may be transmitted to a further data processing appliance by way of the data communication interface 54. Here, the output on the display 16' may be graphical, numerical and/or alphanumerical, for example in the form of a measurement value, a measurement curve, a signal profile, a time profile, as image data or in a gradient display, and also in a combination thereof. Alternatively, or additionally, a representation by means of a signal indicator is possible, in particular by means of e.g. a light-emitting diode, which evaluates a target variable by way of a color coding (e.g. red, yellow, green).

The method repeats during the further examination of the fuel 42a and/or of the oil 42b and/or of the hydraulic fluid 42c, indicated by the arrow 114.

What is claimed is:

1. A method of examining at least one of fuel, oil, and hydraulic fluid with a measuring appliance including an apparatus for energy supply, the method comprising:
   generating a measurement signal with at least a nuclear magnetic resonance sensor of the measuring appliance;
   controlling the measuring appliance with a control apparatus of the measuring appliance;
   evaluating the measurement signal supplied by the nuclear magnetic resonance sensor with an evaluation apparatus of the measuring appliance;
   outputting ascertained information based on the evaluated measurement signal corresponding to an examination of at least one of the fuel, the oil, and the hydraulic fluid with an output apparatus of the measuring appliance;
   using the measuring appliance in a vehicle and during operation of the vehicle; and
   using the ascertained information for open-loop and/or closed-loop control of at least one component of the vehicle.

2. The method according to claim 1, further comprising:
   evaluating the measurement signal supplied by the nuclear magnetic resonance sensor with the evaluation apparatus of the measuring appliance,
   wherein the measurement signal includes a spectrum and/or a relaxation time of the measurement signal resulting from the excitation of nuclear spins in the fuel and/or oil and/or hydraulic fluid examined by the nuclear magnetic resonance sensor.

3. The method according to claim 1, further comprising:
   comparing the ascertained information with reference data from a reference database with the evaluation apparatus,
   wherein the ascertained information includes a spectrum and/or a relaxation time.

4. The method according to claim 1, further comprising:
   displaying the ascertained information with a display of the output apparatus,
   wherein the ascertained information includes a spectrum and/or a relaxation time, and/or a deviation of ascertained information from reference data from a reference database.

5. The method according to claim 1, further comprising:
   calibrating the measuring appliance using a tetramethylsilane sample provided within the appliance before examining the fuel and/or the oil and/or hydraulic fluid.

6. The method according to claim 1, further comprising:
   using the measuring appliance directly on a fuel-conducting and/or oil-conducting and/or hydraulic-fluid-conducting component of the vehicle.

7. The method according to claim 1, further comprising:
   displaying at least one of the ascertained information and a deviation of ascertained information from reference data in a reference database at and/or in an operator's platform,
   wherein the ascertained information includes a spectrum and/or a relaxation time.

8. A measuring appliance for a vehicle, comprising:
   a nuclear magnetic resonance sensor;
   a control apparatus configured to control the measuring appliance;
   an evaluation apparatus configured to evaluate a measurement signal supplied by the nuclear magnetic resonance sensor;
   an output apparatus configured to output ascertained information based on the evaluated measurement signal; and
   an apparatus for energy supply,
   wherein at least one of the nuclear magnetic resonance sensor and the evaluation apparatus is configured to examine at least one of fuel, oil, and hydraulic fluid of the vehicle, and
   wherein the ascertained information is used for open-loop and/or closed-loop control of at least one component of the vehicle.

9. A method for examining at least one of fuel, oil, and hydraulic fluid of a vehicle with a measuring appliance in the vehicle, comprising:
   calibrating a nuclear magnetic resonance sensor of the measuring appliance using a tetramethylsilane sample provided within the appliance;
   measuring at least one spectrum and/or one relaxation time resulting from an excitation of nuclear spins in at least one of the fuel, the oil, and the hydraulic fluid of the vehicle;
   evaluating measurement signals from the nuclear magnetic resonance sensor by comparing the measurement signals with reference data from a reference database;
   outputting the evaluation results, including at least one of ascertained information and a deviation of ascertained information from reference data of a reference database; and
   using the ascertained information for open-loop and/or closed-loop control of at least one component of the vehicle.

* * * * *